(12) United States Patent
Shaohui et al.

(10) Patent No.: US 10,666,933 B2
(45) Date of Patent: May 26, 2020

(54) 3D IMAGE DISPLAY DEVICE AND METHOD

(71) Applicant: Samsung Electronics Co., Ltd., Suwon-si (KR)

(72) Inventors: Jiao Shaohui, Beijing (CN); Zhou Mingcai, Beijing (CN); Hong Tao, Beijing (CN); Li Weiming, Beijing (CN); Wang Haitao, Beijing (CN); Dong Kyung Nam, Suwon-si (KR); Wang Xiying, Beijing (CN)

(73) Assignee: Samsung Electronics Co., Ltd., Suwon-si (KR)

( * ) Notice: Subject to any disclaimer, the term of this patent is extended or adjusted under 35 U.S.C. 154(b) by 63 days.

(21) Appl. No.: 15/326,594

(22) PCT Filed: May 14, 2015

(86) PCT No.: PCT/KR2015/004822
§ 371 (c)(1),
(2) Date: Jan. 16, 2017

(87) PCT Pub. No.: WO2016/010246
PCT Pub. Date: Jan. 21, 2016

(65) Prior Publication Data
US 2017/0208323 A1    Jul. 20, 2017

(30) Foreign Application Priority Data

Jul. 16, 2014  (CN) .......................... 2014 1 0338749
Apr. 30, 2015  (KR) ........................ 10-2015-0061078

(51) Int. Cl.
*H04N 13/395*  (2018.01)
*H04N 13/305*  (2018.01)
(Continued)

(52) U.S. Cl.
CPC ......... *H04N 13/395* (2018.05); *H04N 5/2226* (2013.01); *H04N 13/122* (2018.05);
(Continued)

(58) Field of Classification Search
CPC ........... H04N 13/0495; H04N 13/0404; H04N 13/0484; A61B 6/022; G06T 19/20; G06G 5/377
(Continued)

(56) References Cited

U.S. PATENT DOCUMENTS 8,411,932 B2   4/2013 Liu et al.
2003/0198377 A1*  10/2003 Ng ........................... G06K 9/20
                                                              382/154
(Continued)

FOREIGN PATENT DOCUMENTS

EP         2 490 451 A1    8/2012
KR    10-2012-0122042 A   11/2012
(Continued)

OTHER PUBLICATIONS

International Search Report dated Jul. 24, 2015 in counterpart PCT/KR2015/004822 (5 pages in Korean with English Translation).

*Primary Examiner* — Thai Q Tran
*Assistant Examiner* — Syed Y Hasan
(74) *Attorney, Agent, or Firm* — NSIP Law

(57) ABSTRACT

3D image display device and method are provided. The 3D image display device divides a first 3D image into multiple depth layers, determines irregular pixels corresponding to the divided depth layers, generates second 3D images corresponding to the depth layers, respectively, using the corresponding irregular pixels, and synthesizes the generated images, thereby providing a final high-resolution 3D image.

16 Claims, 9 Drawing Sheets

(51) Int. Cl.
  *H04N 13/351* (2018.01)
  *H04N 13/383* (2018.01)
  *H04N 13/122* (2018.01)
  *H04N 5/222* (2006.01)
  *A61B 6/02* (2006.01)
  *G06T 15/00* (2011.01)
(52) U.S. Cl.
  CPC ......... *H04N 13/305* (2018.05); *H04N 13/351* (2018.05); *H04N 13/383* (2018.05); *A61B 6/022* (2013.01); *G06T 15/00* (2013.01)
(58) Field of Classification Search
  USPC ........ 348/51, 59; 378/41; 382/154; 345/419, 345/428
  See application file for complete search history.

(56) References Cited

U.S. PATENT DOCUMENTS

| | | | |
|---|---|---|---|
| 2005/0041781 A1* | 2/2005 | Jefferson | G06T 11/006 378/210 |
| 2007/0171290 A1 | 7/2007 | Kroger | |
| 2010/0118045 A1 | 5/2010 | Brown Elliott et al. | |
| 2013/0106844 A1* | 5/2013 | Hong | G06T 15/04 345/419 |
| 2013/0135293 A1 | 5/2013 | Kim et al. | |
| 2013/0208099 A1 | 8/2013 | Ohmi | |
| 2014/0146148 A1* | 5/2014 | Maciocci | H04N 13/0484 348/59 |
| 2014/0192044 A1 | 7/2014 | Hwang et al. | |
| 2015/0097837 A1* | 4/2015 | Jepsen | G06F 3/1446 345/428 |

FOREIGN PATENT DOCUMENTS

| | | |
|---|---|---|
| KR | 10-1220098 B1 | 1/2013 |
| KR | 10-1239058 B1 | 3/2013 |
| KR | 10-2013-0060598 A | 6/2013 |
| KR | 10-2014-0004115 A | 1/2014 |
| KR | 10-2014-0053721 A | 5/2014 |
| KR | 10-2014-0065894 A | 5/2014 |
| WO | WO 2010/048632 A1 | 4/2010 |
| WO | WO 2010/091901 A1 | 8/2010 |

* cited by examiner 3D image

FIG. 9

| Regular pixel | 10mm (CDP) | 40mm | 50mm | 70mm | 90mm | 100mm | 110mm |
|---|---|---|---|---|---|---|---|
| MTF irregular pixel | 0.7 | 0.64 | 0.46 | 0.36 | 0.35 | 0.345 | 0.34 |
| MTF content depth | 0.7 | 0.66 | 0.55 | 0.485 | 0.5 | 0.53 | 0.54 |
| growth ratio | 0% | 3.125% | 19.565% | 34.72% | 42.857% | 53.623% | 58.824% |

3D IMAGE DISPLAY DEVICE AND METHOD

CROSS-REFERENCE TO RELATED APPLICATIONS

This application is a U.S. National Stage Application of International Application No. PCT/KR2015/004822, filed on May 14, 2015, which claims the benefit under 35 USC 119(a) and 365(b) of Chinese Patent Application No. 201410338749.7, filed on Jul. 16, 2014, in the State Intellectual Property Office of the People's Republic of China, and Korean Patent Application No. 10-2015-0061078, filed on Apr. 30, 2015, in the Korean Intellectual Property Office, the entire disclosures of which are incorporated herein by reference for all purposes.

BACKGROUND

1. Field

The following description relate to a method and apparatus for displaying a three-dimensional (3D) image using an irregular pixel.

2. Description of Related Art

A naked eye three-dimensional (3D) display apparatus includes a display panel to display a high-resolution two-dimensional (2D) interlaced image and a light direction modulation element, such as, for example, a micro-lens array (MLA) to refract the interlaced image in a different direction, thereby providing a 3D image to be viewed by naked eyes, without a need to wear glasses. In the interlaced image including multi-view image information, adjacent pixels may display image information at different angles. Each image may need to be separated through a refraction of a lens to provide a clear 3D image. However, a crosstalk effect may occur in the adjacent pixels. Due to the crosstalk effect, 3D images overlap each other, which may lead to a degradation in resolution. When the multi-view image is separated through the refraction of the lens, a ray of light may also be diffused in a process of propagating the ray of light radiated from a pixel. In this situation, the adjacent pixels may be interfered with in response to a change in a beam area, which may also lead to a degradation in resolution.

Accordingly, in the naked eye 3D display system, a depth of field (DOF) may be restricted due to a characteristic that the ray of light is physically propagated, and the resolution may be changed based on a depth layer.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In one general aspect, there is provided an apparatus for displaying a three-dimensional (3D) image, the apparatus including a depth layer divider configured to divide a first 3D image into depth layers, a pixel determiner configured to determine irregular pixels respectively corresponding to the depth layers, a 3D image generator configured to generate second 3D images respectively corresponding to the depth layers using the determined irregular pixels, and a 3D image compositor configured to composite the second 3D images.

The depth layer divider may be configured to divide the first 3D image into the depth layers using a depth peeling algorithm.

The pixel determiner may be configured to set depth planes based on an optical characteristic of a microlens array, and to determine the irregular pixels corresponding to the depth layers according to a depth plane to which a depth layer of the depth layers belongs.

The apparatus may include a contour detail feature extractor configured to extract a contour detail feature from the first 3D image and to analyze a frequency direction and a frequency magnitude of the contour detail feature, wherein the pixel determiner may be configured to determine the irregular pixels corresponding to the depth layers based on any one or any combination of a frequency direction of the contour detail feature corresponding to each of the depth layers, a frequency magnitude of the contour detail feature corresponding to the each of the depth layers, and the depth planes to which the depth layers respectively belong.

The 3D image generator may be configured to render multi-view images using the determined irregular pixels respectively corresponding to the depth layers based on multi-view image information, to rearrange pixels with respect to the rendered multi-view images, and to generate the second 3D images respectively corresponding to the depth layers.

The multi-view image information may include any one or any combination of viewpoint position information and gaze field angle information.

The 3D image compositor may be configured to determine a back-and-forth location relationship in a depth direction for different portions of the second 3D images, and to composite the second 3D images in an order from a deepest layer based on the determined back-and-forth location relationship.

The pixel determiner may be configured to select an irregular pixel for each of the depth layers from irregular pixels set in advance.

The irregular pixels may each be a pixel block including adjacent regular pixels or sub-pixels.

The irregular pixels may be different from the regular pixels in shape and size.

In another general aspect, there is provided a method of displaying a three-dimensional (3D) image, the method including dividing a first 3D image into depth layers, determining irregular pixels respectively corresponding to the depth layers, generating second 3D images respectively corresponding to the depth layers using the determined irregular pixels, and compositing the generated second 3D images.

The dividing may include dividing the first 3D image into the depth layers using a depth peeling algorithm.

The determining may include setting depth planes based on an optical characteristic of a microlens array, and determining the irregular pixels respectively corresponding to the depth layers according to a depth plane to which a depth layer of the depth layers belongs.

The method may include extracting a contour detail feature from the first 3D image and determining a frequency direction and a frequency magnitude of the contour detail feature, wherein the determining of the irregular pixels may include determining the irregular pixels corresponding to the depth layers based on any one or any combination of a frequency direction of the contour detail feature corresponding to each of the depth layers, a frequency magnitude of the contour detail feature corresponding to the each of the depth layers, and the depth planes to which the depth layers respectively belong.

The generating may include rendering a plurality of multi-view images using the determined irregular pixels respectively corresponding to the depth layers based on multi-view image information, rearranging pixels with respect to the rendered multi-view images, and generating the second 3D images respectively corresponding to the depth layers.

The multi-view image information may include any one or any combination of viewpoint position information and gaze field angle information.

The compositing may include determining a back-and-forth location relationship in a depth direction for different portions of the second 3D images, and compositing the second 3D images in an order from a deepest layer based on the determined back-and-forth location relationship to acquire a final 3D image.

The determining may include selecting an irregular pixel for each of the depth layers from irregular pixels set in advance.

The irregular pixels may be each a pixel block comprises adjacent regular pixels or sub-pixels.

The irregular pixels may be different from the regular pixels in shape and size.

Other features and aspects will be apparent from the following detailed description, the drawings, and the claims.

BRIEF DESCRIPTION OF DRAWINGS

FIG. 9 illustrates an example of an result of an analysis performed by comparing an MTF value obtained through a display test using irregular pixels to an MTF value obtained through a display test using regular pixels.

Figure 1:
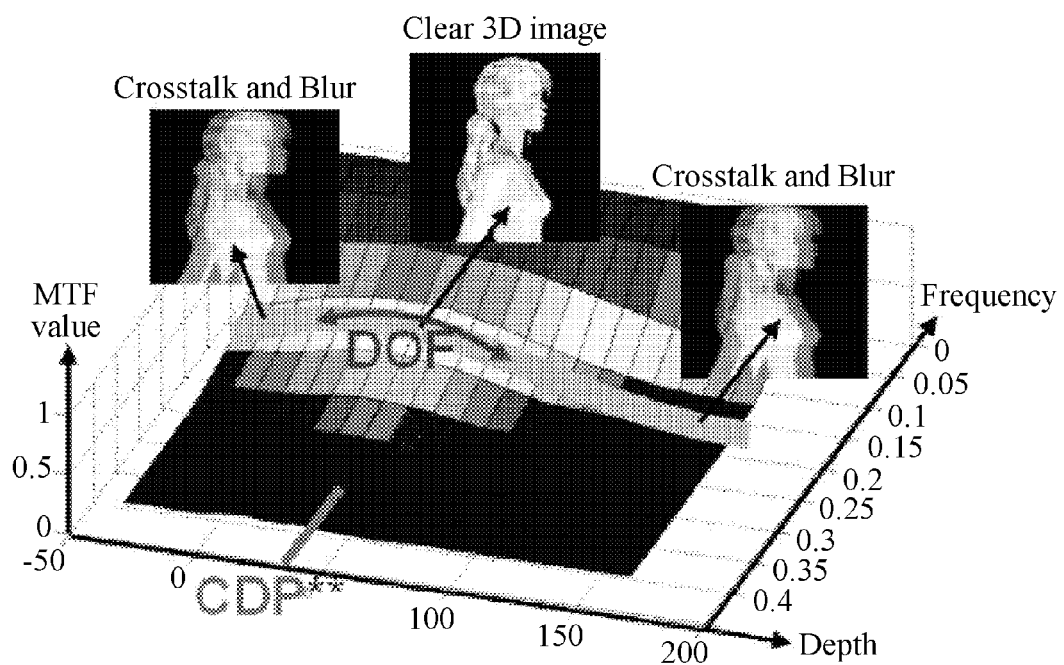
FIG. 1 illustrates an example of a modulation transfer function (MTF) to estimate a display resolution.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or apparatuses described herein. However, various changes, modifications, and equivalents of the methods, apparatuses, and/or apparatuses described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or apparatuses described herein that will be apparent after an understanding of the disclosure of this application.

FIG. 1 illustrates an example of a modulation transfer function (MTF) to estimate a display resolution. In an example, a performance of a naked-eye three-dimensional (3D) display apparatus is measured based on a display resolution and a depth of field (DOF) of a 3D image. For example, the display resolution of the 3D image is quantized using an MTF. The MTF may measure a resolution based on a number of lines in a range of about 1 millimeter (mm), and may be defined as, "MTF value=(Maximal value of illuminance−Minimal value of illuminance)/(Maximal value of illuminance+Minimal value of illuminance)". In an example, the MTF value is a value between 0 and 1. For example, the greater the MTF value, the higher the resolution of the 3D image that is currently displayed, and the lesser the MTF value, the lower the resolution of the 3D image.

A graph of FIG. 1 represents an MTF of a 3D image displayed based on a sinusoidal grating. In the graph, an X-axial direction represents a depth value of the 3D image, a Y-axial direction represents a frequency, and a Z-axial direction represents an MTF value. In an example, the sinusoidal grating includes different frequencies and different depth planes. In an example of FIG. 1, a resolution is determined based on a central depth plane (CDP). The resolution is maximized on the CDP, and the resolution decreases according to an increase in a distance from the CDP, which may lead to a crosstalk error and a blur effect. In other words, in the naked-eye 3D display apparatus, the DOF of the displayed 3D image may be restricted due to a physical light propagation characteristic.

Accordingly, an issue of the physical light propagation characteristic such as crosstalk may need to be solved to provide a high-resolution 3D image in a naked-eye 3D display apparatus.

Figure 2:
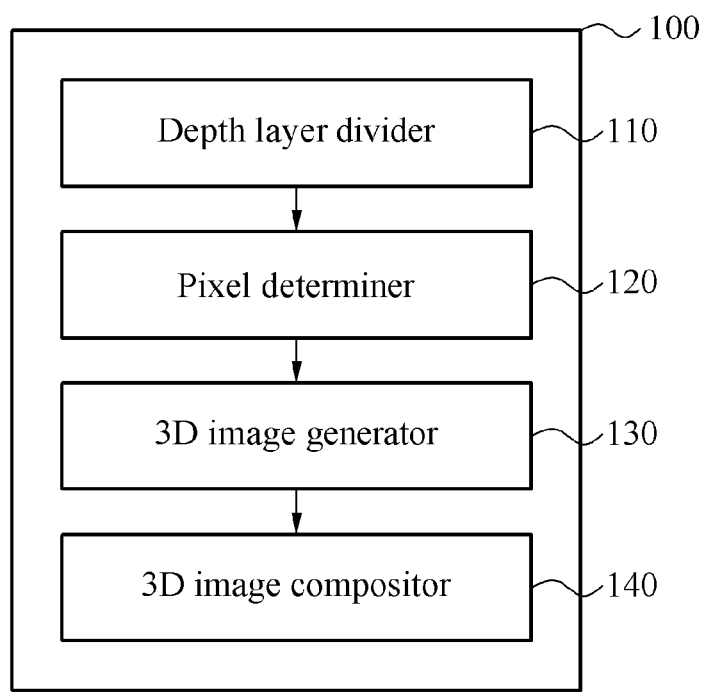
FIG. 2 is a diagram illustrating an example of a three-dimensional (3D) image display apparatus.

FIG. 2 is a diagram illustrating an example of a 3D image display apparatus 100. Referring to FIG. 2, the 3D image display apparatus 100 includes a depth layer divider 110, a pixel determiner 120, a 3D image generator 130, and a 3D image compositor 140.

In an example, the depth layer divider 110 divides a first 3D image corresponding to a desired image to be displayed into a plurality of depth layers. For example, the depth layer divider 110 divides the first 3D image into a number of depth layers using a depth peeling algorithm. In an example, the number of depth layers are predetermined.

In an example, the depth layer divider 110 converts a pixel included in the first 3D image into a fragment. For example, a pixel including a horizontal coordinate value x and a vertical coordinate value y is converted into a pixel including the horizontal coordinate value x, the vertical coordinate value y, and a depth-directional coordinate value z, i.e., the fragment. In an example, the depth-directional coordinate value z indicates a depth may be a depth value of the pixel corresponding to the fragment. Hereinafter, the depth value of the pixel corresponding to the fragment may also be referred to as the depth value of the fragment. The depth layer divider 110 may arrange fragments in a depth direction based on a depth value of each of the fragments, generate a plurality of depth layers based on a result of depth arrangement and a preset number of depth layers, and output the generated depth layers. For example, when a 3D image having a maximal depth value is 4 and a minimal depth value is −4 is divided into four depth layers, a fragment having a depth value between 2 and 4 may be divided as a first depth layer, a fragment having a depth value between 0 and 2 may be divided as a second depth layer, a fragment having a depth value between −2 and 0 may be divided as a third depth layer, and a fragment having a depth value between −4 and −2 may be divided as a fourth depth layer. Through this, a plurality of depth layers may be obtained to be output. The number of depth layers and a DOF of each of the depth layers may be varied without departing from the spirit and scope of the illustrative examples described. In the foregoing example, a fragment having a depth value between 3 and 4 may also be divided as the first depth layer, a fragment having a depth value between 0 and 3 may also be divided as the second depth layer, a fragment having a depth value between −3 and 0 may also be divided as the third depth layer, and a fragment having a depth value between −3 and −4 may also be divided as the fourth depth layer.

Figure 3A:
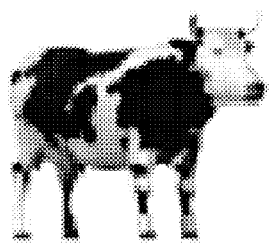
FIG. 3 illustrates an example of a result of depth peeling.
Figure 3B:
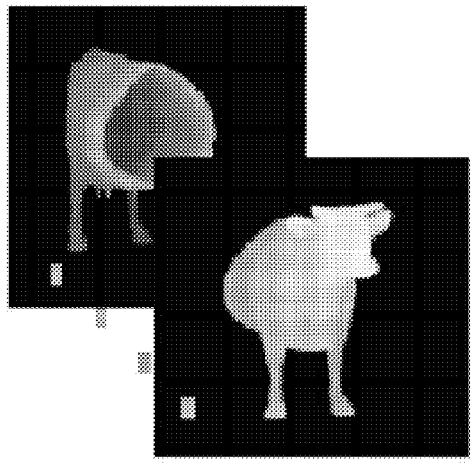

FIG. 3 illustrates an example of a result of depth peeling. As illustrated in FIG. 3, a depth peeling may be performed on a 3D image of FIG. 3A using the depth layer divider 110 to form a plurality of depth layers, as shown in of FIG. 3B. Through this, each of the depth layers may represent a portion corresponding to the 3D image.

The depth layer divider 110 is configured to divide a 3D image to be displayed into a plurality of depth layers using a depth peeling algorithm in the present example, other algorithms may be used without departing from the spirit and scope of the illustrative examples described. For example, a salience mapping method may be applied to the depth layer division.

Referring back to FIG. 2, the pixel determiner 120 determines irregular pixels respectively corresponding to depth layers obtained by the depth layer divider 110. A plurality of depth planes, which is a plurality of DOFs, may be set based on an optical characteristic of a light direction modulation element of the 3D image display apparatus 100, i.e., a microlens array included in a 3D image display apparatus. For example, a CDP of FIG. 1 may be set to be a first depth layer, a plane on which a depth other than a depth corresponding to the CDP in a display of the 3D image display apparatus 100 is located may be set to be a second depth plane, and a plane on which a depth other than that of the display DOF of the 3D image display apparatus 100 is located may be set to be a third depth plane. In an example, the pixel determiner 120 determines depth planes to which the depth layers belong based on the DOFs of the depth layers, and determine irregular pixels respectively corresponding to the depth layers based on the depth planes.

In an example, a predetermined depth layer L included in the depth layers will be described. When the depth layer L belongs to the first depth plane, i.e., the CDP, an image displayed on a display plane may need to have a maximal resolution such that a 3D image portion corresponding to the depth layer is displayed using general regular pixels. When the depth layer L belongs to the second depth plane, that is, the plane on which the depth other than the depth corresponding to the CDP in the display DOF of the 3D image display apparatus 100 is located, or belongs to the third depth plane, i.e., the plane on which the depth other than that of the display DOF of the 3D image display apparatus 100, the pixel determiner 120 determined an irregular pixel corresponding to the depth layer L.

Figure 4:
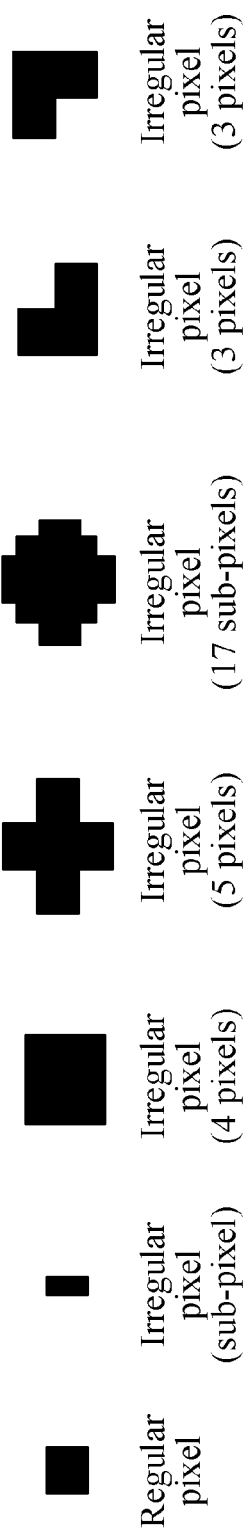
FIG. 4 illustrates an example of irregular pixels.

FIG. 4 illustrates an example of irregular pixels. The irregular pixels may be a pixel block including a plurality of adjacent regular pixels or sub-pixels and different from the regular pixels in shape and size. For example, a plurality of irregular pixels may be set in advance, and the pixel determiner 120 may select at least one irregular pixel for a depth layer L from the preset irregular pixels. In an example, the pixel determiner 120 may compare resolutions obtained when a 3D image portion corresponding to the depth layer L is displayed using various types of irregular pixels and determine which irregular pixel is to be used. The pixel determiner 120 may selectively determine the irregular pixel to be used by comparing the resolutions obtained when the 3D image portion corresponding to the depth layer L is displayed using a combination of at least two types of irregular pixels among the preset irregular pixels. In an example, the pixel determiner 120 combines adjacent regular pixels or sub-pixels to form a plurality of candidate irregular pixels in different shape and size. Using the candidate irregular pixels, in an example, the pixel determiner 120 determines a resolution of a 3D image portion corresponding to the depth layer L, and determines a candidate irregular pixel corresponding to a maximal resolution to be a final irregular pixel corresponding to the depth layer L.

In the foregoing, determining irregular pixels using a depth applying method, i.e., determining irregular pixels respectively corresponding to depth layers based on a depth plane to which each of the depth layer belongs is described, embodiments are not limited thereto and other methods may be used without departing from the spirit and scope of the illustrative examples described.

In an example, the irregular pixels of the depth layers are determined using a frequency applying method. The irregular pixels of the depth layers are determined based on a frequency feature, for example, a direction and a magnitude of a frequency of a 3D image to be displayed. The 3D image display apparatus 100 may include a contour detail feature extractor (not shown) to extract a contour detail feature from a first 3D image and determine a frequency magnitude and a direction of the contour detail feature, i.e., a frequency direction. In an example, the pixel determiner 120 determines the irregular pixels corresponding to the depth layers based on any one or any combination of the direction of the contour detail feature corresponding to each of the depth layers, i.e., a contour detail feature of a pixel corresponding to a depth layer, and the frequency magnitude of the contour detail feature corresponding to each of the depth layers such that different widths in different frequency directions are implemented in a result thereof, for example, a pixel width being inversely proportional to the frequency magnitude.

A contour detail feature included in a 3D image may be extracted using various methods, such as, for example, multi-scale Gabor filtering without departing from the spirit and scope of the illustrative examples described. Thus, related descriptions will be omitted.

In an example, the pixel determiner 120 determines the irregular pixels corresponding to the depth layers using both depth applying method and frequency applying method. The pixel determiner 120 determines the irregular pixels respectively corresponding to the depth layers based on at least one of the direction of the contour detail feature corresponding to each of the depth layers, the frequency magnitude corresponding to each of the depth layers, and the depth plane to which each of the depth layer belongs.

Although the divided depth layers and the set depth planes differ in DOF, in an example, the depth layer divider 110 may use depth layers and depth planes having the same DOF in a process of depth layer division.

Referring back to FIG. 1, the 3D image generator 130 generates second 3D images respectively corresponding to the depth layers using the irregular pixels respectively corresponding to the depth layers determined by the pixel determiner 120.

In an example, the 3D image generator 130 renders a plurality of multi-view images using the irregular pixels corresponding to the determined depth layers based on multi-view image information of the 3D image display apparatus 100. In an example, the 3D image generator 130 performs pixel rearrangement on the rendered multi-view images, thereby generating the second 3D images corresponding to the depth layers. In an example, the multi-view image information may include at least one of viewpoint position information and field angle information and may be a value corresponding to a hardware performance parameter setting of the 3D image display apparatus 100. Each of the multi-view images may correspond to a single viewpoint and a single field angle position.

Rendering the multi-view images and performing the pixel rearrangement on the multi-view images may be performed by any of the various methods, and thus, related descriptions will be omitted. without departing from the spirit and scope of the illustrative examples The 3D image compositor 140 may composite the plurality of second 3D images respectively corresponding to the plurality of depth layers generated by the 3D image generator 130, thereby acquiring a final 3D image.

In an example, the 3D image compositor 140 determines a back-and-forth location relationship in a depth direction with respect to different portions of the plurality of second 3D images respectively corresponding to the plurality of depth layers generated by the 3D image generator 130. The 3D image compositor composites the plurality of second 3D images in an order from a deepest layer, for example, covering from the back to front, based on the determined back-and-forth location relationship, thereby acquiring the final 3D image. When compositing the second 3D images, the compositing may be performed in an order from a 3D image of the deepest depth layer. In an example an image of each location included in the final 3D image is determined based on a corresponding location of the second 3D image having a minimal depth among the plurality of second 3D images used to composite the final 3D image.

Figure 5A:
FIGS. 5A and 5B illustrate examples of comparing a 3D image generated by a 3D image display apparatus to a general 3D image.
Figure 5B:
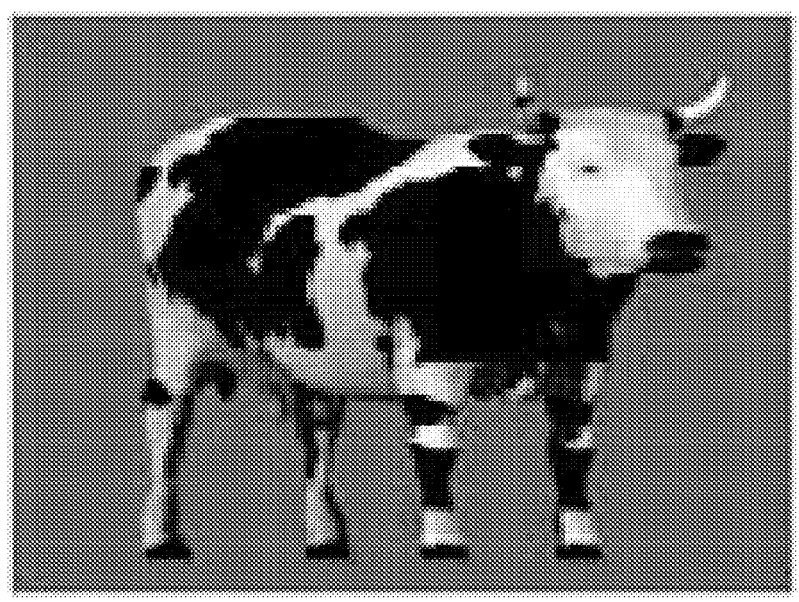

FIG. 5A and 5B illustrate examples of comparing a 3D image generated by the 3D image display apparatus 100 to a general 3D image. FIG. 5A) illustrates a screenshot of a 3D image having a depth and displayed using regular pixels based on general technology, and FIG. 5B illustrates the same 3D image displayed using the 3D image display apparatus 100. As illustrated in FIG. 5, in comparison to a result of displaying the 3D image using the regular pixels based on the general technology, the 3D image generated by the 3D image display apparatus 100 may be displayed with increased resolution and a display DOF.

Figure 6:
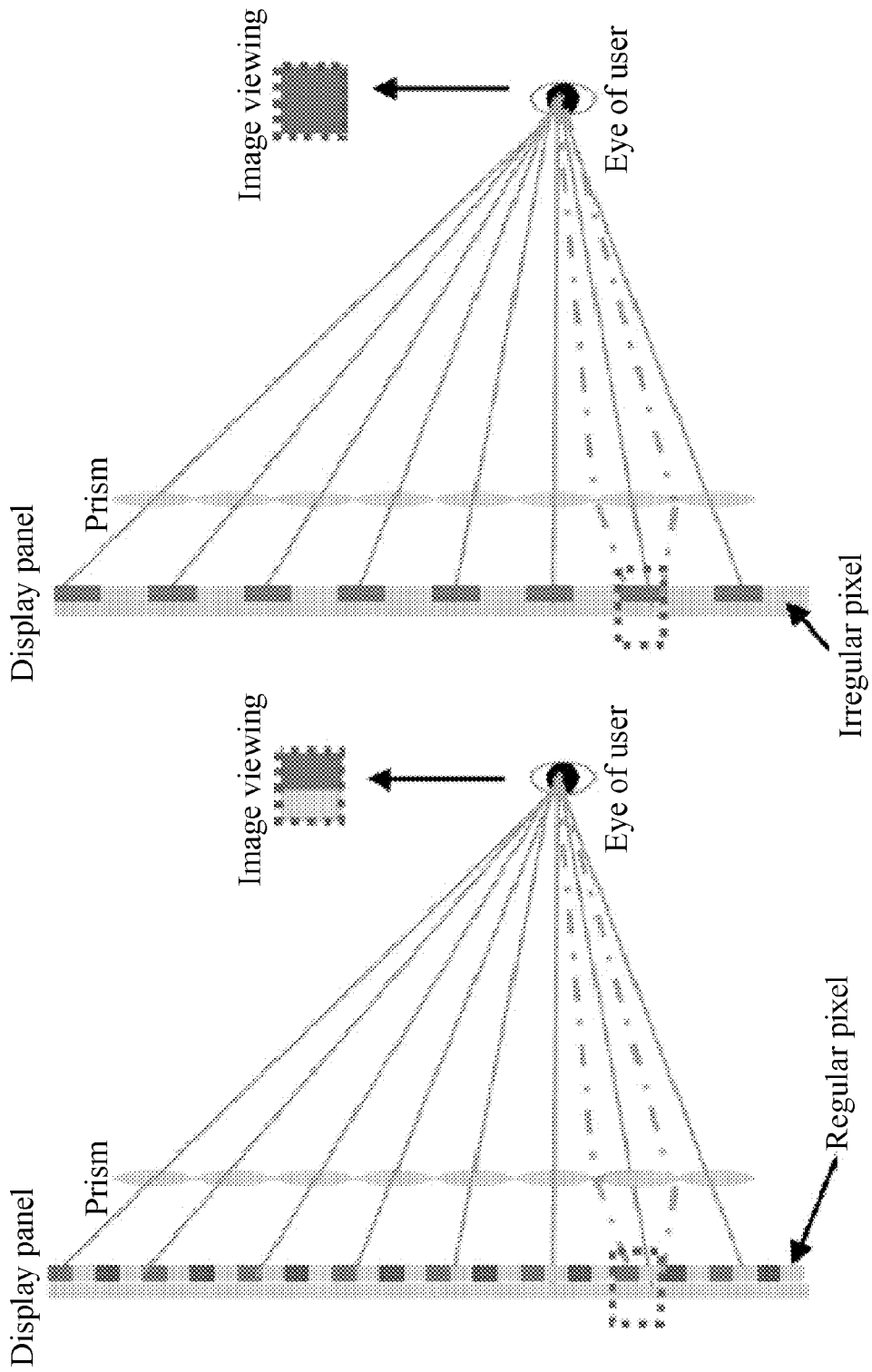
FIG. 6 illustrates a principle of reducing crosstalk by displaying a 3D image based on irregular pixels.

FIG. 6 illustrates an example of reducing crosstalk by displaying a 3D image based on irregular pixels according to an example embodiment. A left portion of FIG. 6 illustrates a screen on which a 3D image is displayed using regular pixels. A general apparatus of displaying a 3D image using regular pixels may be restricted on a hardware design. Thus, a user's eye may observe luminous intensity of two adjacent pixels. In this example, the two pixel may represent different viewpoint images and thus, a crosstalk effect may occur. A right portion of FIG. 6 illustrates an example of displaying a 3D image using irregular pixels. The irregular pixels used in the right portion of FIG. 6 are greater in size than the regular pixels. In this example, the user may observe luminous intensity of one pixel with the eyes at the same location as the left portion of FIG. 6 and thus, the crosstalk effect may not occur. Accordingly, the crosstalk effect occurring in a process of displaying the 3D image may be alleviated.

Figure 7:
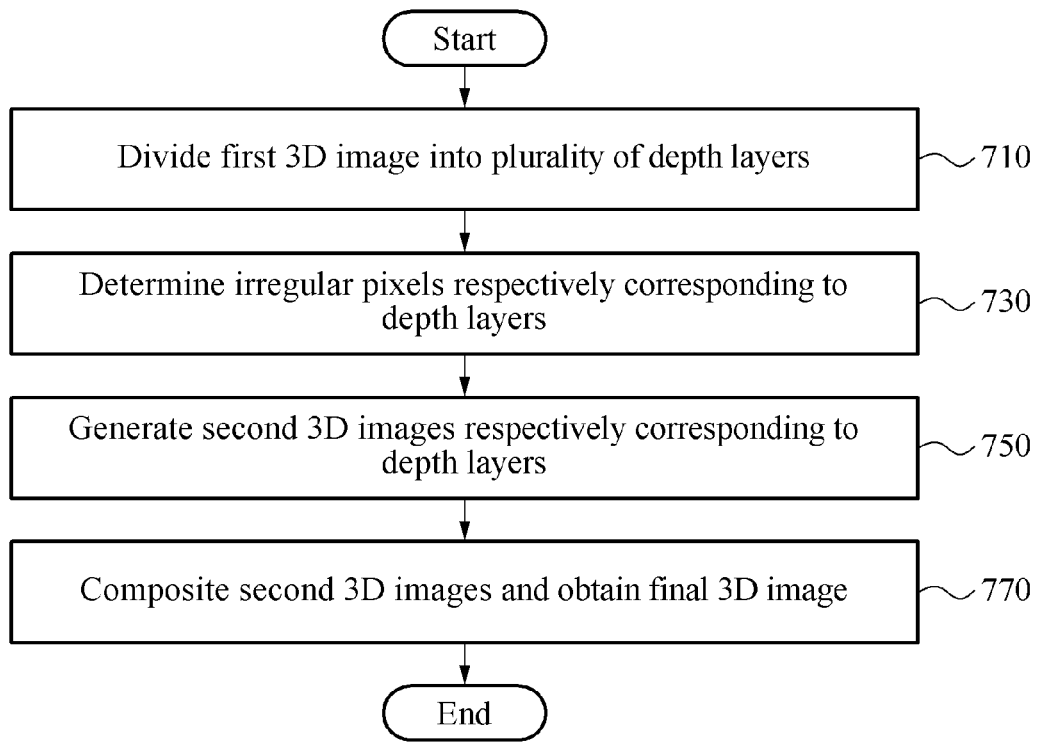
FIG. 7 is a diagram illustrating an example of a method of displaying a 3D image.

FIG. 7 is a diagram illustrating an example of a method of displaying a 3D image. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. In addition to the description of FIG. 7 below, the above descriptions of FIGS. 1-6, are also applicable to FIG. 7, and are incorporated herein by reference. Thus, the above description may not be repeated here.

In 710, the depth layer divider 110 included in the 3D image display apparatus 100 divides a first 3D image into a plurality of depth layers. In an example, depth layer divider 110 divides a 3D image into a plurality of depth layers using a depth peeling algorithm. A pixel included in the first 3D image may be converted into a fragment, i.e., a pixel including a horizontal coordinate value x and a vertical coordinate value y may be converted into a pixel including the horizontal coordinate value x, the vertical coordinate value y, and a depth-directional coordinate value z corresponding to a depth value of the pixel, i.e., the fragment. Thus, fragments may be arranged in a depth direction based on a depth value of each of the fragment. Based on a result of depth arrangement and the preset number of depth layers, a plurality of depth layers may be generated and output.

In 730, the pixel determiner 120 included in the 3D image display apparatus 100 determines irregular pixels corresponding to the depth layers into which the first 3D image is divided by the depth layer divider 110. The irregular pixels may each be a pixel block including a plurality of adjacent regular pixels or sub-pixels. In this example, the irregular pixels may be different from the regular pixels in shape and size. An operation of determining irregular pixels may select at least one irregular pixel for each of the depth layers from a plurality of irregular pixels set in advance.

In an example, a plurality of depth planes may be set based on an optical characteristic of a microlens array, which is a light direction modulation element of the 3D image display apparatus 100. An operation of determining the irregular pixels may determine irregular pixels respectively corresponding to depth layers based on a depth plane to which each of the depth layers belongs. The descriptions of FIG. 2 are also applicable here, and are incorporated herein by reference. Thus, the above description with respect to a method of setting a depth plane to which a depth layer belongs and determining irregular pixels based on the depth plane may not be repeated here.

In 730, the irregular pixels of the depth layers may be determined based on a frequency characteristic, such as, for example, a direction and a magnitude of a frequency of the first 3D image. Operation 730 may include an operation of extracting a contour detail feature from the first 3D image and determining a frequency direction and a frequency magnitude of the contour detail feature. In this example, operation 730 determines the irregular pixels respectively corresponding to the depth layers based on at least one of the frequency direction of the contour detail feature corresponding to each of the depth layers, the frequency magnitude of the contour detail feature corresponding to each of the depth layers, and the depth planes to which the depth layers respectively belong.

In 750, the 3D image generator 130 included in the 3D image display apparatus 100 generates second 3D images respectively corresponding to the depth layers using the irregular pixels respectively corresponding to the depth layers determined in operation 730. In an example, a plurality of multi-view images are rendered using the irregular pixels respectively corresponding to the depth layers determined in operation 730 based on multi-view image information of the 3D image display apparatus 100, and pixel arrangement may be performed on the rendered multi-view images. Through this, 3D images corresponding to the depth layers may be generated. In an example, the multi-view image information may include at least one of viewpoint location information and gaze field angle information.

In 770, the 3D image compositor 140 of the 3D image display apparatus 100 composites the second 3D images to obtains a final 3D image. For example, a back-and-forth location relationship in a depth direction may be determined with respect to different portions of the second 3D images generated in operation 750. Based on the determined back-and-forth location relationship, the second 3D images may be composited in an order from a deepest layer. Through this, the final 3D image may be obtained.

Figure 8:
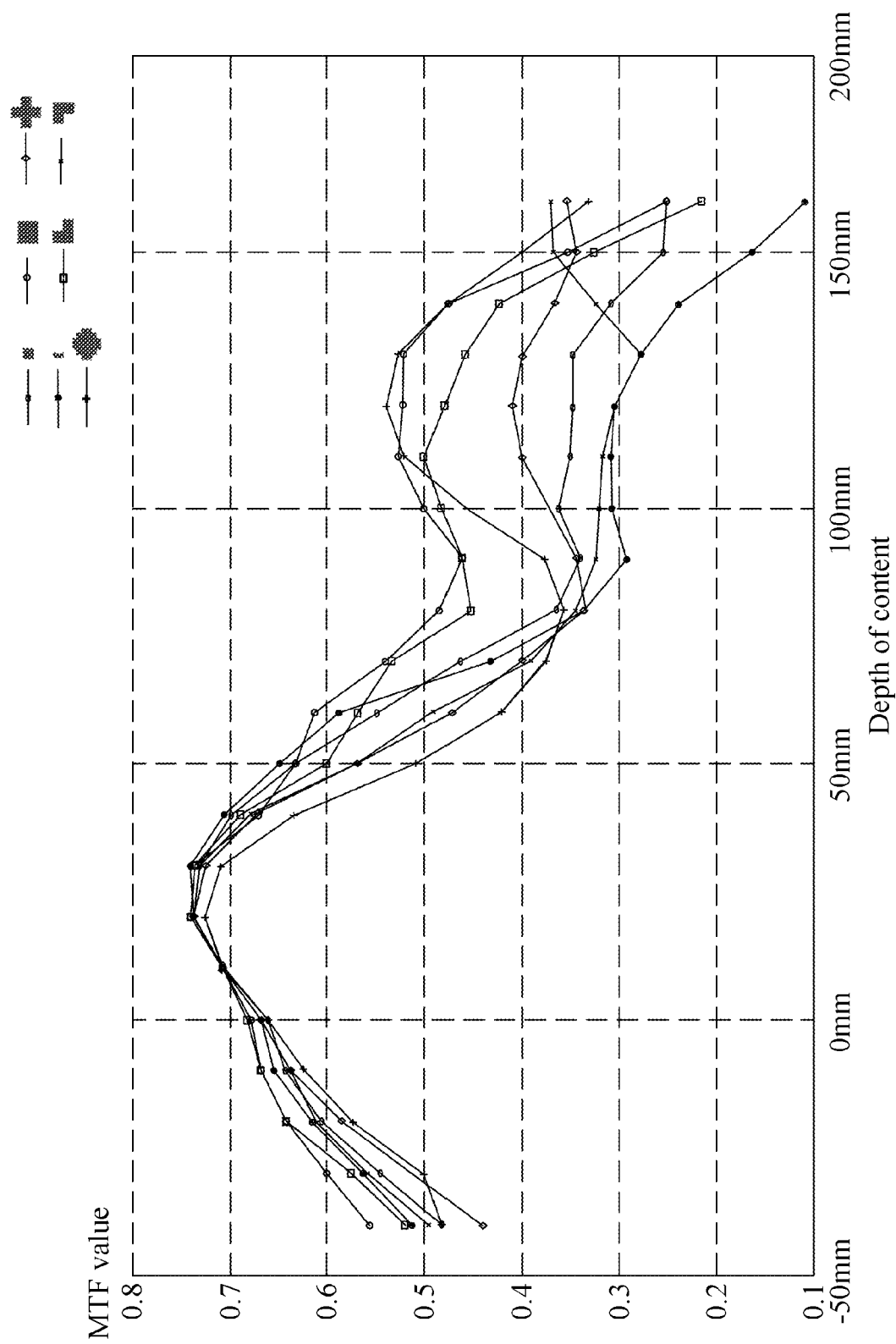
FIG. 8 is a diagram illustrating an example of MTF value obtained through a display test conducted based on different irregular pixels using a 3D image display apparatus.

FIG. 8 is a diagram illustrating an example of an MTF value obtained through a display test conducted based on different irregular pixels using a 3D image display apparatus. In FIG. 8, a graph with a symbol " ○ " represents an MTF value obtained through a display using regular pixels and graphs with other symbols represent MTF values obtained through a display using irregular pixels.

As illustrated in FIG. 8, irregular pixels having different shapes may correspond to different MTF values. However, it is indicated that most of the irregular pixels enhances a resolution of a portion of depth planes other than the CDP, that is, the depth plane corresponding to the maximal MTF value in the example of FIG. 8.

FIG. 9 illustrates an example of a comparison of an MTF value obtained through a display test using irregular pixels to an MTF value obtained through a display test using regular pixels. In FIG. 9, a test frequency may be 0.097 period/mm. As illustrated in FIG. 9, using irregular pixels, a resolution may increase according to an increase in a distance from a CDP while a depth is 10 mm.

Accordingly, the 3D image display apparatus and method may solve a crosstalk error, enhance a resolution of a 3D display, increase a DOF of a 3D image to be displayed, and increase a speed of processing the 3D image. Also, manufacturing costs of the 3D image display apparatus may be reduced.

The 3D image display apparatus 100, pixel determiner 120, 3D image generator 130, 3D image compositor 140, and other units and apparatuses described in the FIGS., for example FIG. 1, which perform the operations described in this application are implemented by hardware components configured to perform the operations described in this application. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIG. 7 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. An apparatus for displaying a three-dimensional (3D) image, the apparatus comprising:
 a depth layer divider configured to divide a first 3D image into depth layers;
 a pixel determiner configured to determine different irregular pixels corresponding to each of the depth layers;
 a 3D image generator configured to generate second 3D images respectively corresponding to the depth layers using the determined irregular pixels; and
 a 3D image compositor configured to composite the second 3D images,
 wherein each of the irregular pixels comprises either one or both of a pixel block including a plurality of adjacent regular pixels and a sub-pixel, and
 wherein the irregular pixels are different from the regular pixels in shape and size.

2. The apparatus of claim 1, wherein the depth layer divider is further configured to divide the first 3D image into the depth layers using a depth peeling algorithm.

3. The apparatus of claim 1, wherein the pixel determiner is further configured to set depth planes based on an optical characteristic of a microlens array, and to determine the irregular pixels corresponding to the depth layers according to a depth plane to which a depth layer of the depth layers belongs.

4. The apparatus of claim 3, further comprising:
 a contour detail feature extractor configured to extract a contour detail feature from the first 3D image and to analyze a frequency direction and a frequency magnitude of the contour detail feature,
 wherein the pixel determiner is further configured to determine the irregular pixels corresponding to the depth layers based on any one or any combination of a frequency direction of the contour detail feature corresponding to each of the depth layers, a frequency magnitude of the contour detail feature corresponding to the each of the depth layers, and the depth planes to which the depth layers respectively belong.

5. The apparatus of claim 1, wherein the 3D image generator is further configured to render multi-view images using the determined irregular pixels respectively corresponding to the depth layers based on multi-view image information, to rearrange pixels with respect to the rendered multi-view images, and to generate the second 3D images respectively corresponding to the depth layers.

6. The apparatus of claim 5, wherein the multi-view image information comprises any one or any combination of viewpoint position information and gaze field angle information.

7. The apparatus of claim 1, wherein the 3D image compositor is further configured to determine a back-and-forth location relationship in a depth direction for different portions of the second 3D images, and to composite the second 3D images in an order from a deepest layer based on the determined back-and-forth location relationship.

8. The apparatus of claim 1, wherein the pixel determiner is further configured to select an irregular pixel for each of the depth layers from irregular pixels set in advance.

9. A method of displaying a three-dimensional (3D) image, the method comprising:
 dividing a first 3D image into depth layers;
 determining different irregular pixels corresponding to each of the depth layers;
 generating second 3D images respectively corresponding to the depth layers using the determined irregular pixels; and
 compositing the generated second 3D images,
 wherein each of the irregular pixels comprises either one or both of a pixel block including a plurality of adjacent regular pixels and a sub-pixel, and
 wherein the irregular pixels are different from the regular pixels in shape and size.

10. The method of claim 9, wherein the dividing comprises dividing the first 3D image into the depth layers using a depth peeling algorithm.

11. The method of claim 9, wherein the determining comprises setting depth planes based on an optical characteristic of a microlens array, and determining the irregular pixels respectively corresponding to the depth layers according to a depth plane to which a depth layer of the depth layers belongs.

12. The method of claim 11, further comprising:
 extracting a contour detail feature from the first 3D image and determining a frequency direction and a frequency magnitude of the contour detail feature,
 wherein the determining of the irregular pixels comprises determining the irregular pixels corresponding to the depth layers based on any one or any combination of a frequency direction of the contour detail feature corresponding to each of the depth layers, a frequency magnitude of the contour detail feature corresponding to the each of the depth layers, and the depth planes to which the depth layers respectively belong.

13. The method of claim 9, wherein the generating comprises rendering a plurality of multi-view images using the determined irregular pixels respectively corresponding to the depth layers based on multi-view image information, rearranging pixels with respect to the rendered multi-view images, and generating the second 3D images respectively corresponding to the depth layers.

14. The method of claim 13, wherein the multi-view image information comprises any one or any combination of viewpoint position information and gaze field angle information.

15. The method of claim 9, wherein the compositing comprises determining a back-and-forth location relationship in a depth direction for different portions of the second 3D images, and compositing the second 3D images in an order from a deepest layer based on the determined back-and-forth location relationship to acquire a final 3D image.

16. The method of claim 9, wherein the determining comprises selecting an irregular pixel for each of the depth layers from irregular pixels set in advance.

* * * * *